United States Patent
Pallikaris

(10) Patent No.: US 11,672,699 B2
(45) Date of Patent: Jun. 13, 2023

(54) SYSTEM FOR CORRECTING AN IRREGULAR SURFACE OF A CORNEA AND USES THEREOF

(71) Applicant: Ioannis Pallikaris, Crete (GR)

(72) Inventor: Ioannis Pallikaris, Crete (GR)

(*) Notice: Subject to any disclaimer, the term of this patent is extended or adjusted under 35 U.S.C. 154(b) by 416 days.

(21) Appl. No.: 16/780,500

(22) Filed: Feb. 3, 2020

(65) Prior Publication Data

US 2020/0170835 A1    Jun. 4, 2020

Related U.S. Application Data

(62) Division of application No. 15/377,508, filed on Dec. 13, 2016, now Pat. No. 10,548,768.

(60) Provisional application No. 62/395,793, filed on Sep. 16, 2016.

(51) Int. Cl.
| | | |
|---|---|---|
| *A61F 9/008* | (2006.01) | |
| *A61F 9/007* | (2006.01) | |
| *A61N 5/06* | (2006.01) | |
| *A61L 27/52* | (2006.01) | |
| *A61L 27/24* | (2006.01) | |

(52) U.S. Cl.
CPC ............. *A61F 9/007* (2013.01); *A61F 9/008* (2013.01); *A61F 9/00825* (2013.01); *A61F 9/00827* (2013.01); *A61L 27/24* (2013.01); *A61L 27/52* (2013.01); *A61N 5/062* (2013.01); *A61F 2009/00872* (2013.01); *A61L 2430/16* (2013.01)

(58) Field of Classification Search
CPC .............................................. A61F 9/007–009
See application file for complete search history.

(56) References Cited

U.S. PATENT DOCUMENTS

| | | | | |
|---|---|---|---|---|
| 5,279,611 A | * | 1/1994 | McDonnell | A61F 9/00819 606/4 |
| 5,492,135 A | * | 2/1996 | DeVore | C08L 89/06 522/68 |
| 6,589,558 B1 | | 7/2003 | Pallikaris | |
| 2010/0049174 A1 | | 2/2010 | Kuehnert et al. | |
| 2010/0210996 A1 | | 8/2010 | Peyman | |

(Continued)

OTHER PUBLICATIONS

Yang E, Roberts CJ, Mehta JS, A Review of Corneal Biomechanics after LASIK and SMILE and the Current Methods of Corneal Biomechanical Analysis. J Clin Exp Ophthalmol, 2015, 6:507.

(Continued)

*Primary Examiner* — Eugene T Wu
(74) *Attorney, Agent, or Firm* — Benjamin Aaron Adler

(57) ABSTRACT

Provided are systems and methods for correcting a corneal surface irregularity surface in a subject. The system generally comprises a infrared laser, for example, and infrared laser and a laser control unit, a corneal contacting unit, a gel solidifying unit and an electronic device tangibly storing algorithms to operate the units. In the methods, a polymerizable or thermo-reversible gel or polymerized resin is applied to the anterior corneal surface and solidified as a layer over the cornea. A first correcting cut is lasered into the stroma of an applanated cornea, the gel layer is then removed and a second correcting cut is lasered in the stroma of the applanated cornea. The lenticule formed intrastromaly by the first and second correcting cuts is removed such that the cornea has a corrected corneal curvature.

7 Claims, 6 Drawing Sheets

(56) References Cited

U.S. PATENT DOCUMENTS

2013/0237970 A1  9/2013  Summers et al.

OTHER PUBLICATIONS

Sekundo et al. "Small incision corneal refractive surgery using the small incision lenticule extraction (SMILE) procedure for the u correction of myopia and myopic astigmatism: results of a 6 month prospective study." Br J Ophthalmol. Mar. 2011;95(3):335-9.

* cited by examiner

SYSTEM FOR CORRECTING AN IRREGULAR SURFACE OF A CORNEA AND USES THEREOF

CROSS-REFERENCE TO RELATED APPLICATIONS

This application is a divisional under 35 U.S.C. § 120 of pending non-provisional application U.S. Ser. No. 15/377,508, filed Dec. 13, 2016, which claims benefit of priority under 35 U.S.C. § 119(e) to provisional application U.S. Ser. No. 62/395,793, filed Sep. 16, 2016, now abandoned, the entirety of which is hereby incorporated by reference.

BACKGROUND OF THE INVENTION

Field of the Invention

The present invention generally relates to the field of ophthalmology. More specifically, the present invention relates to a system for smoothing an irregular surface of a cornea during an opthalmological surgery, such as a femto refractive surgery.

Description of the Related Art

Femto refractive surgery has become fairly common in recent years for its high accuracy and low risk approaches. Over the past decades, the systems along with the operation procedures have been significantly improved to maximize the efficacy and minimize the side effects of this type of surgeries.

For example, Kuehnert et al. in U.S. Pat. No. 8,491,575 B2 describes a laser system and the correcting apparatus for generating a correcting cut surface in the cornea of an eye to correct ametropia. The system comprises a laser unit to emit pulsed laser radiation, a control unit for control of the laser unit, as well as a contact element releasably coupled to the laser unit and specifically adapted for the respective correcting cut surface. The pulse duration is, for example, within the femtosecond range (e.g. 50 to 800 fs), with a pulse repetition rate of between 10 and 500 kHz.

The pulsed laser radiation is focused through the contact element into the cornea of an eye. Focusing is effected by two deflecting mirrors that form a movable scanner and by the optics. Scanning occurs under the control of the control unit, so that basically any desired locations in the cornea can be exposed to the pulsed laser radiation. The control unit controls the laser unit such that an optical breakthrough is generated at the respective focus position in the cornea to separate tissue. The focus positions are selected to be adjacent to each other such that a desired cut surface is present in the cornea.

The laser unit and control unit disclosed in U.S. Pat. No. 8,491,575 can be utilized, for example, in the same manner as in a conventional laser keratome, such as used in the so-called LASIK method (laser in situ keratomileusis) to cut a thin lamella (often referred to also as flap) which is unilaterally detached from the cornea. Thus, the optics, merely represented as a lens, can comprise several optical elements are suitably arranged along the beam path from the laser up to the contact element. For example, the apparatus may further comprise at least a third contact element, which imposes a further curvature upon the anterior corneal surface when contacting the latter, the further curvature deviating from the standard curvature as well as from the actual curvature of the second contact element, and thus has the effect that a cut surface generated using the standard setting results in a further correcting cut surface.

Moreover, the contact surface of the corresponding contact element defining the actual curvature may be flexible. The flexibility is selected such that minor irregularities can be compensated for although on average the actual curvature is imposed upon the anterior corneal surface. This has the advantageous effect that the correcting cut surface to be generated has an extremely smooth profile. However, while the flexibility may be achieved, for example, by a thin, flexible layer, e.g. a gel layer, forming the contact surface, which is in turn applied to a contact element carrier that is rigid with respect to the cornea, the flexible layer disclosed in U.S. Pat. No. 8,491,575 is pre-molded and has limited ability to deform in situ to fit into the corneal surface irregularities.

Therefore, there is a recognized need in the art for an opthalmological surgical system and method that comprises a gel layer that fills the irregularities on the anterior surface of a cornea. Particularly, the prior art is deficient in an opthalmologically useful gel to smooth the irregularities in a femto refractive surgery. The present invention fulfills this long-standing need and desire in the art.

SUMMARY OF THE INVENTION

The present invention is directed to a system for smoothing an irregular corneal surface of an eye to correct vision in a subject. The system comprises a laser unit comprising a pulsed laser emitter and a laser control unit in electronic communication with the laser unit. A corneal contacting unit is in electronic communication with the laser control unit and is positionable proximate to a corneal surface. A gel solidifying unit is configured to initiate a polymerization or a thermo-reversible solidification of a gel composition. An electronic device comprising a processor and a memory tangibly stores an algorithm comprising processor-executable instructions configured to operate the units.

The present invention also is directed to a method for smoothing an irregular surface of a cornea in an eye prior to an ophthalmological surgical procedure. The method comprises applying a polymerizable or thermo-reversible gel to an anterior corneal surface of the eye and molding the gel over the anterior corneal surface. The gel is solidified, via the gel solidifying unit comprising the system described herein, as a layer covering the anterior corneal surface, thereby smoothing irregularities present in the corneal surface.

The present invention is directed further to a method for performing a surgical procedure to correct a defect in eyesight of a subject. The method comprises forming a solidified gel layer of a minimum thickness over an anterior corneal surface of an eye via the system described herein. A first correcting surface cut is lasered on the cornea through the solidified gel layer and the solidified gel layer is removed. The anterior corneal surface of the eye is contacted with a second contact element. A vacuum is applied to form a second curvature defined by the contacting surface of the second contact element to the anterior surface of the cornea. A second surface cut is lasered when the vacuum is applied where the second surface cut intersects the first correcting surface cut such that a lenticule is formed in the cornea. The lenticule is removed from the cornea to form a corrected corneal curvature thereby correcting the defect in eyesight of the subject.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
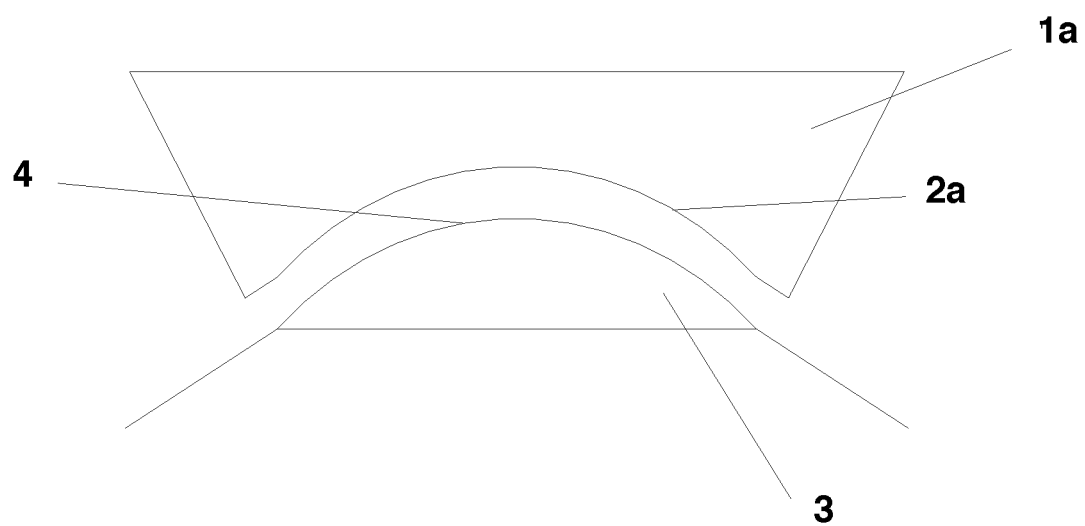
FIG. 1 is a schematic representation of the positioning of a contact element with respect to the anterior corneal surface prior to applanation of the cornea.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "lenticule" refers to the area on a cornea formed when correcting surface cuts and standard surface cuts are made on the anterior corneal surface of an eye. Removing the so formed lenticule creates a desired curvature of the cornea that corrects a defect in eyesight.

As used herein, the term "subject" refers to a recipient of the methods to correct a defect in vision via the systems described herein. Preferably, the subject is a human.

In one embodiment of the present invention, there is provided a system for smoothing an irregular corneal surface of an eye to correct vision in a subject, comprising a laser unit comprising a pulsed laser emitter; a laser control unit in electronic communication with the laser unit; a corneal contacting unit in electronic communication with the laser control unit positionable proximate to a corneal surface; a gel solidifying unit configured to initiate a polymerization or a thermo-reversible solidification of a gel composition; and an electronic device comprising a processor and a memory tangibly storing an algorithm comprising processor-executable instructions to operate the units.

In this embodiment the laser emitter may be configured to pulse laser radiation within a femtosecond range with a frequency of about 10 Hz to about 500 kHz. Also, the laser control unit may be configured to control a duration, positioning and intensity of the emitted pulsed laser radiation. In addition the algorithm may comprise processor-executable instructions to identify a curvature to achieve a desired final corneal curvature.

Also in this embodiment an example of a polymerizable gel may be polyurethane methacrylate (PUMA). In another example the polymerizable gel comprises a polyester and a catalyst Methyl Ethyl Ketone Peroxide (MEKP). In yet another example, the polymerizable gel may be a hydrogel. In addition in this embodiment, a thermo-reversible gel composition may comprise a soluble collagen solution. Examples of the collagen are a porcine collagen, a bovine collagen or a combination thereof.

In one aspect of this embodiment the corneal contacting unit may comprise a first contact element having a concave contacting surface removably contactable with an anterior corneal surface with the gel composition applied thereon; a second contact element having a concave contacting surface removably contactable with an anterior corneal surface without the gel applied thereon; and a vacuum applicator disposed on the second contact element configured to produce a curvature of the anterior corneal surface corresponding to the concave contacting surface. In this aspect, when a mean corneal index is about 1.4 Diopters, a difference of a corneal refractive index between the cornea and a solidified gel composition is less than about 0.5 Diopter.

In another aspect the gel solidifying unit may comprise an ultraviolet light emitter configured for triggering a polymerization of a polymerizable gel composition; a cooling unit configured for solidifying a thermos-reversible gel composition by cooling or a combination thereof; a liquid emitter configured to apply a catalyst on a solidified polymerized resin; or a combination thereof. Further to this aspect, the gel solidifying unit may comprise an applicator configured to apply the gel composition between the anterior corneal surface and the contacting surface of the corneal contacting unit.

In another embodiment of the present invention there is provided a method for smoothing an irregular surface of a cornea in an eye prior to an ophthalmological surgical procedure, comprising the steps of applying a polymerizable or thermo-reversible gel to an anterior corneal surface of the eye; molding the gel over the anterior corneal surface; and solidifying the gel via the gel solidifying unit comprising the system as described supra as a layer covering the anterior corneal surface, thereby smoothing irregularities present in the anterior corneal surface.

In one aspect of this embodiment the applying step may comprise delivering via an applicator a minimum amount of the gel onto the corneal surface.

In another aspect the molding step may comprise selecting a first contact element having a concave surface curvature corresponding to a curvature effective to correct a defect in eyesight; and positioning the contact element on the cornea such that the gel interfaces with the concave surface of the contact element and the anterior corneal surface of the eye.

In yet another aspect the solidifying step may comprise irradiating the polymerizable gel layer with ultraviolet radiation. Alternatively, the solidifying step may comprise cooling the thermo-reversible gel layer. In another alternative, the solidifying step may comprise chemically fixing the gel composition by applying a chemical fixation agent.

In yet another embodiment of the present invention there is provided a method for performing a surgical procedure to correct a defect in eyesight of a subject, comprising the steps of forming a solidified gel layer of a minimum thickness over an anterior corneal surface of an eye via the system as described supra; lasering a first correcting surface cut on the cornea through the solidified gel layer; removing the solidified gel layer; contacting the anterior corneal surface of the eye with a second contact element; applying a vacuum to form a second curvature defined by the contacting surface of the second contact element to the anterior surface of the cornea; lasering a second surface cut when the vacuum is applied, where the second surface cut intersects the first correcting surface cut such that a lenticule is formed on the cornea; and removing the lenticule from the cornea to form a corrected corneal curvature thereby correcting the defect in eyesight of the subject.

In an aspect of this embodiment the step of forming a solidified gel layer may comprise delivering via an applicator a minimum amount of a polymerizable gel, a polymerized resin or a thermo-reversible gel onto the corneal surface; positioning a first contact element on the cornea such that the gel interfaces with a concave contacting surface of the first contact element and the anterior corneal surface of the eye; and irradiating the polymerizable gel layer with ultraviolet radiation or cooling the thermo-reversible gel or chemically modifying the polymerized resin, thereby solidifying the gel. In this aspect the prior to the positioning step, the method may comprise applying an algorithm to identify a first curvature corresponding to the first surface cut and a second curvature corresponding to the second surface cut; selecting a first contact element having a contacting surface curvature corresponding to the first curvature; and selecting a second contact element having a contacting surface curvature corresponding to the second curvature. Further to these aspects, the method may comprise applying the algorithm to configure a laser to cut the cornea to produce a first cut surface with a curvature corresponding to the first curvature of the selected first contact element, and a second cut surface with a curvature corresponding to the second curvature of the selected second contact element.

In another aspect of this embodiment, the lasering steps may comprise selecting a duration, positioning and intensity of laser radiation; and pulsing the laser radiation within a femtosecond range with a frequency of about 10 Hz to about 500 kHz to produce the first and second cut surfaces.

Provided herein are systems and methods for smoothing an irregular anterior surface of a cornea during an ophthalmological surgical procedure, for example, a femto refractive surgery. Surface smoothing is done by applying a biocompatible composition, such as a polymerizable or thermo-reversible gel or collagen composition, as a layer over the anterior corneal surface of the eye. A vacuum applied to the composition forms a layer of a minimum thickness between the corneal surface and the applanation component of a contact element, such as a concave contacting surface, of the surgical system disposed over the corneal surface. Upon solidification the layer fills any surface irregularities present on the corneal surface and provides a smooth interface. The composition is applied by any suitable means known in the art, for example, but not limited to, a syringe-like applicator.

The biocompatible composition may comprise, but is not limited to, a polymerizable gel, such as polyurethane methacrylate. Alternatively, the biocompatible composition may be a thermally modified gel or thermo-reversible collagen composition. The thermally modified gel may comprise a chemically modified soluble collagen solution and a polymerization agent. Examples of a thermo-reversible collagen composition include, but are not limited to, soluble porcine collagen, bovine collagen or other type of collagen or a combination thereof. Solidification of the composition is initiated by the application of ultraviolet light or cooling as is known in the art. Further the biocompatible composition may comprise a resin polymerized by a catalyst. An example of a polymerized resin is a polyester polymerized by Methyl Ethyl Ketone Peroxide (MEKP).

The system described herein comprises a plurality of units in electronic communication that are configured to produce the smoothing layer and to generate one or more surface cuts in the stroma of the cornea. For example, the system may generally comprise a laser unit with a pulsed laser emitter and a laser control unit. The laser is configured to emit pulsed laser radiation and is controlled by the control unit to generate one or more correcting surface cuts on the corneal stroma to produce a smoothed corneal surface with a final curvature selected to correct one or more defects in a subject's eyesight. In a non-limiting example, the laser radiation may be pulsed with a femtosecond range with a frequency of about 10 Hz to about 500 kHz. The control unit controls at least the duration, positioning and intensity of the emitted pulsed laser radiation.

The corneal contacting unit applanates the solidified layer and/or the anterior corneal surface via the application of a vacuum prior to generating the correcting surface cuts thereon. The contact element comprising the unit provides, with the corneal surface, a boundary for the solidified gel or collagen interface. The system also comprises a gel solidifying unit with which the biocompatible composition is applied and solidified as described herein. For example, the solidifying unit may comprise an ultraviolet light emitter and/or a cooling unit to effect polymerization or solidification.

Generally, the system comprises an electronic device, such as a computer or smart device as are known in the art, having a memory, a processor and at least one network connection, on which to tangibly store one or more algorithms. The algorithm(s) comprise processor-executable instructions that function to or are configured to operate the units comprising the system. Particularly, the algorithm executes to identify a curvature to achieve a final corrected corneal curvature and/or to configure a laser to cut the cornea to produce the first and second cut surfaces with a curvature corresponding to the curvature of the selected contact element.

Also provided are methods of using the described system. For example the system is useful for smoothing an irregular surface of a cornea in an eye prior to an ophthalmological surgical procedure, such as a femto refractive surgery. Moreover, the system provided herein may be used to perform a surgical procedure to correct a defect in eyesight of a subject. As described herein, after producing the solidified smoothing layer over the anterior corneal surface, a final desired curvature may be determined and the correcting surface cuts planned to effect a correction in eyesight. The skilled person well knows that the selection of applanation curvatures and final corrective curvatures depend on the particular subject and their specific defects in vision.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

FIG. 1 depicts a general system without a gel layer or interface disposed between the contact element, such as a flap contact glass 1a of the system and the anterior corneal surface 4. In the surgical system the laser unit and the control unit (not shown) are configured to cut a flap using the flap contact glass 1a. The standard setting is defined here for the flap contact glass 1a which comprises an inner, concavely curved contact surface or flap contact surface 2a that faces or is disposed proximately to the cornea 3. The standard setting for the control unit is adapted to the flap contact glass 1a and to the curvature imposed upon the anterior corneal surface 4 by the flap contact surface 2a, such that the standard surface cut 5 (the dashed line in FIG. 2) can be generated.

Figure 2:
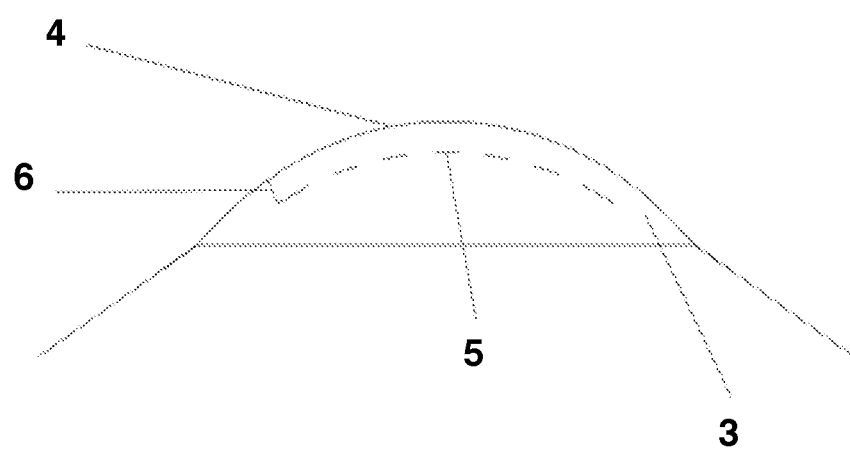
FIG. 2 is a schematic representation of the standard surface cut generated in the cornea during applanation by the contact element using femtolaser technology.

With continued reference to FIG. 1, FIG. 2 illustrates the standard surface cut 5 generated during a cutting operation once the anterior corneal surface 4 has the standard curvature predetermined by the flap contact surface 2a of the flap contact glass 1a. The standard surface cut 5 is generated such the distance from the cut surface to the anterior corneal surface 4 is constant. In order to create the desired cut, an opening cut 6 extending substantially perpendicular from the anterior corneal surface is made. In FIG. 2, the profile of the anterior corneal surface 4 is depicted with a natural curvature without the irregularities, such as a recess, that occur in an actual cornea. Thus, the standard surface cut 5 generated relative to the corneal surface 4, known as a reference surface, is depicted with the same curvature. The standard surface cut 5 described in FIG. 2 is not representative of a desired correcting surface cut to correct defective eyesight (ametropia), but serves to characterize the standard setting for the control unit.

Figure 3:
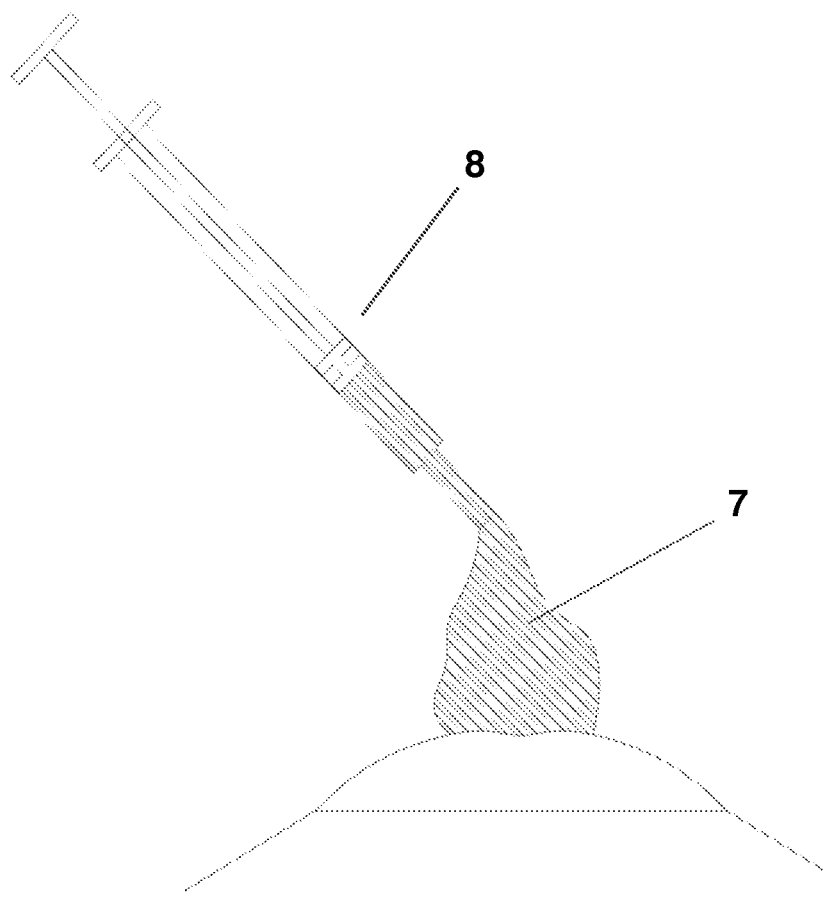
FIG. 3 is a schematic representation of the application of an amount of gel over a corneal surface irregularity.

FIG. 3 illustrates how a small quantity of a suitable gel 7 is applied to the cornea. A syringe-like or other type of gel applicator 8 enables a user to control the amount and placement of the composition onto the anterior corneal surface.

Figure 4:
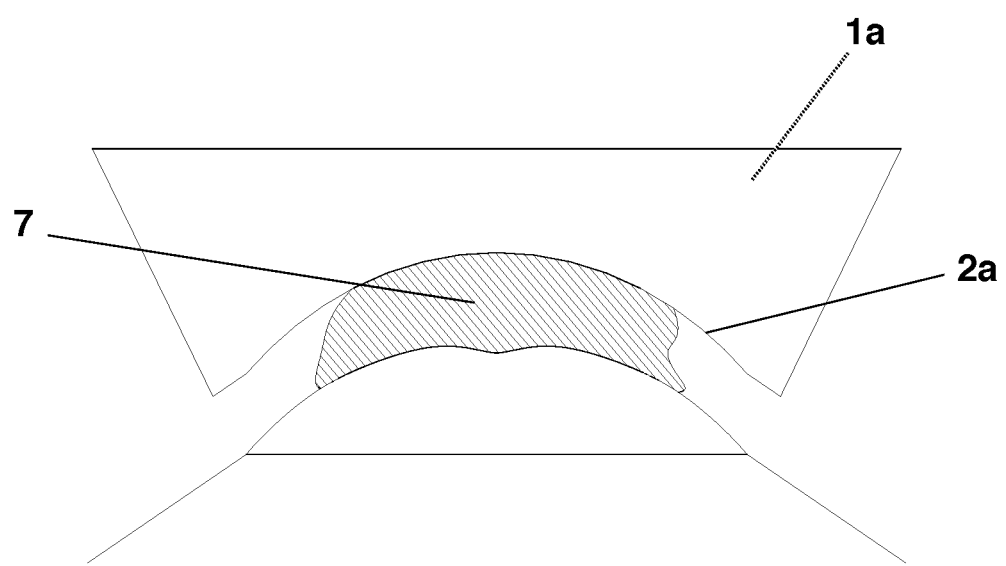
FIG. 4 is a schematic representation of the placement of the contact element for molding the gel.

FIG. 4 shows that the flap contact glass, known as the first contact element 1a, is positioned over and in contact with the applied gel 7. The contact surface 2a works as a molding surface to mold the applied gel over and into the irregularities on the anterior corneal surface.

Figure 5:
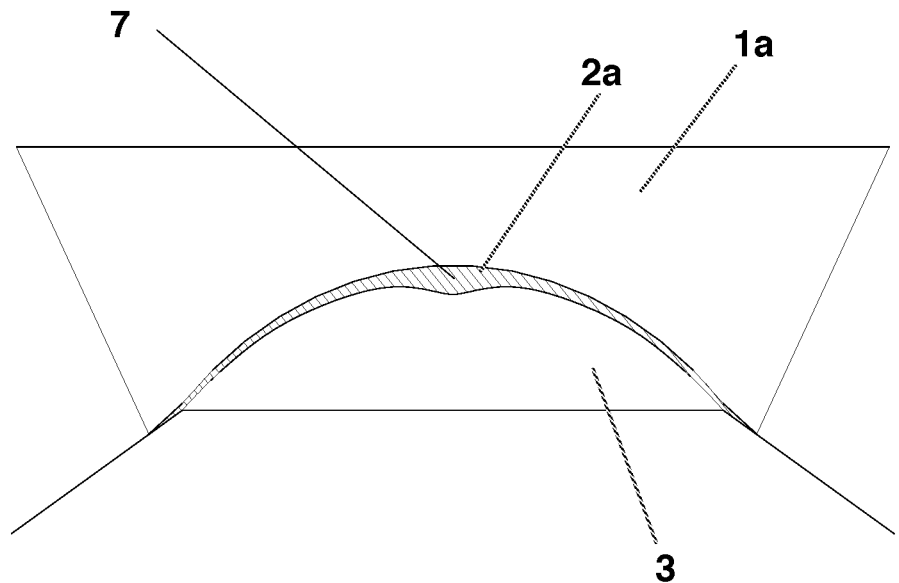
FIG. 5 is a schematic representation of the use of a contact element to form a gel layer of a minimum thickness between the irregular corneal surface and the contacting surface of the contact element.

FIG. 5 illustrates how the flap contact surface 2a creates a new surface over the anterior corneal surface with a minimal quantity of gel 7 filling the space between the corneal surface and the molding surface of the first contact element 1a. The gel 7 imposes an actual curvature upon the cornea 3, which is modified as compared to the standard curvature. For this purpose preoperative corneal topography or keratometry data can be utilized to predetermine the given corneal surface curvature for the correction of the irregularities including the ammetropia. In general, methods similar to these used for contact lens fitting can be used for flap contact glass selection. For vision correcting, the use of a flap contact glass, or first contact element 1a, that optimally fits the to be treated cornea 3 is imperative. The flap contact glass 1a may be selected from a series of pre-existent flap contact glasses.

Figure 6:
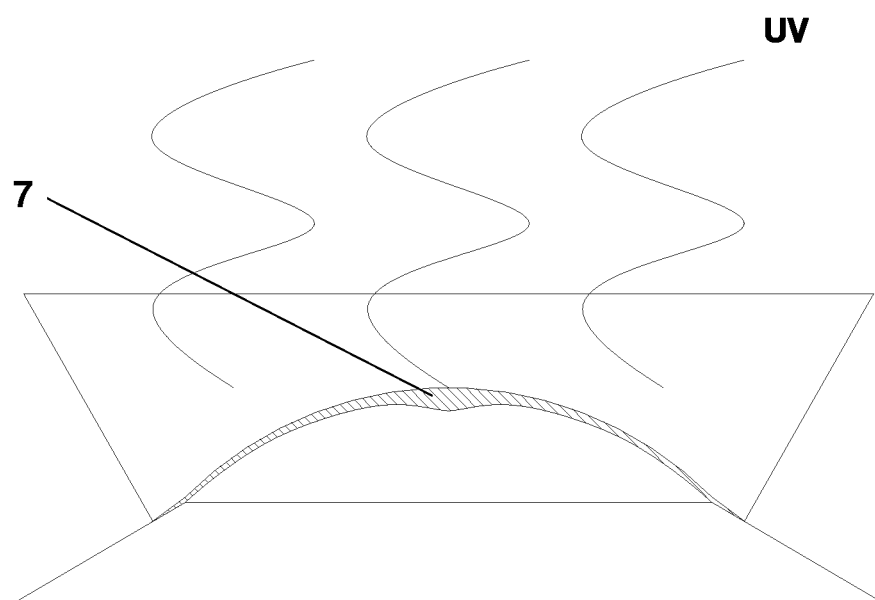
FIG. 6 is a schematic representation of the application of UV radiation for solidification of the gel.

With continued reference to FIG. 5, FIG. 6 illustrates the polymerization of a polymerizable gel to form the gel layer 7 as a layer of minimum thickness over the irregular corneal surface after positioning of the flap contact glass. The delivery of ultraviolet (UV) radiation initiates polymerization of the gel. The polymerized gel layer or interface smooths out the corneal irregularities.

Figure 7:
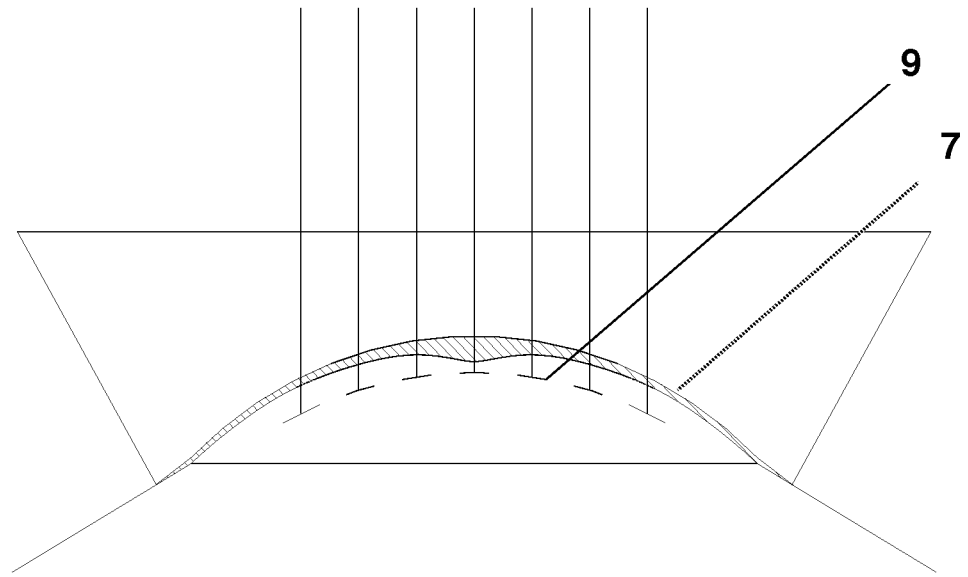
FIG. 7 is a schematic representation of creating the first correcting cut into the stroma using a femto-laser beam.

FIG. 7 depicts the first correcting surface cut 9 illustrated by a dotted line. The first correcting cut through the polymerized gel layer is generated by pulses in a femtosecond range of laser radiation via the laser and laser control units (not shown) using the standard setting as known in the art.

Figure 8:
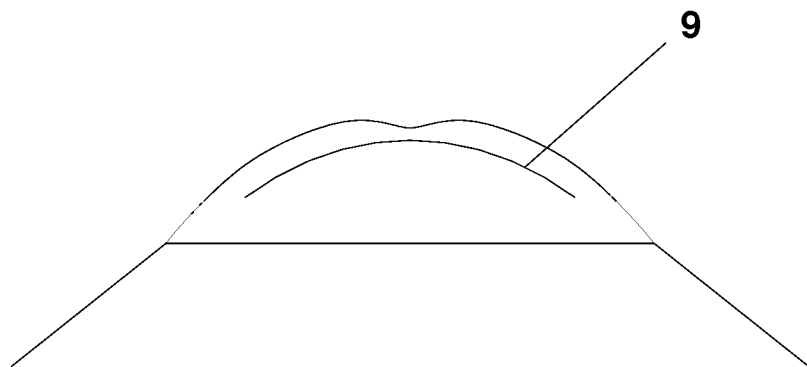
FIG. 8 is a schematic representation of the cornea and first correcting surface cut after removal of the gel.

FIG. 8 depicts first correcting cut surface 9 after the femtosecond laser cut is completed after the first contact element 1a (see FIG. 7) and the remaining polymerized gel layer (see FIG. 7) are removed from the cornea.

Figure 9:
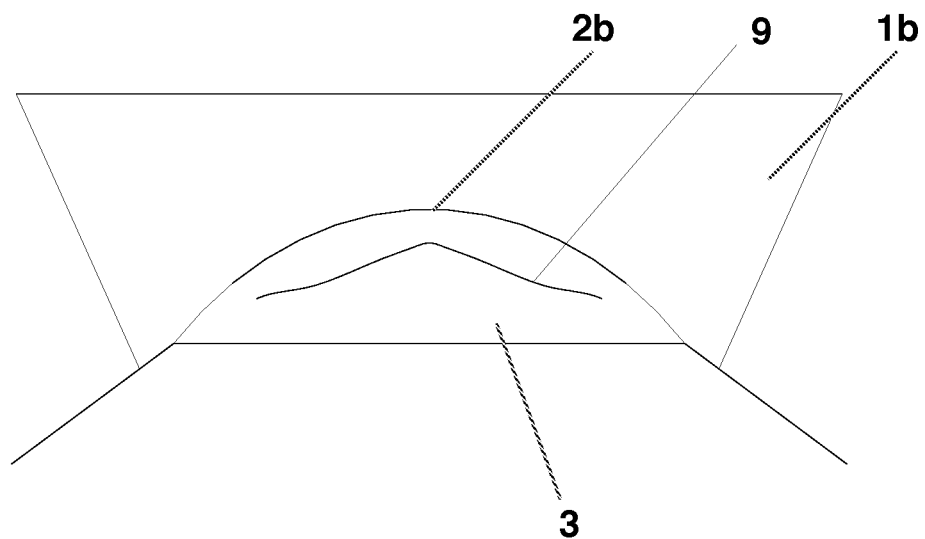
FIG. 9 is a schematic representation of the contact element in contact with the cornea and first correcting cut after applying a vacuum without a gel layer.

FIG. 9 illustrates how the second flap contact glass, know as the second contact element 1b, is positioned on the first correcting cut surface 9 of the cornea 3 after the first correcting cut is made. Vacuum, which is applied on the second contact element, is used to fit the first correcting cut surface on the cornea to contact surface or molding surface 2b without the gel.

Figure 10:
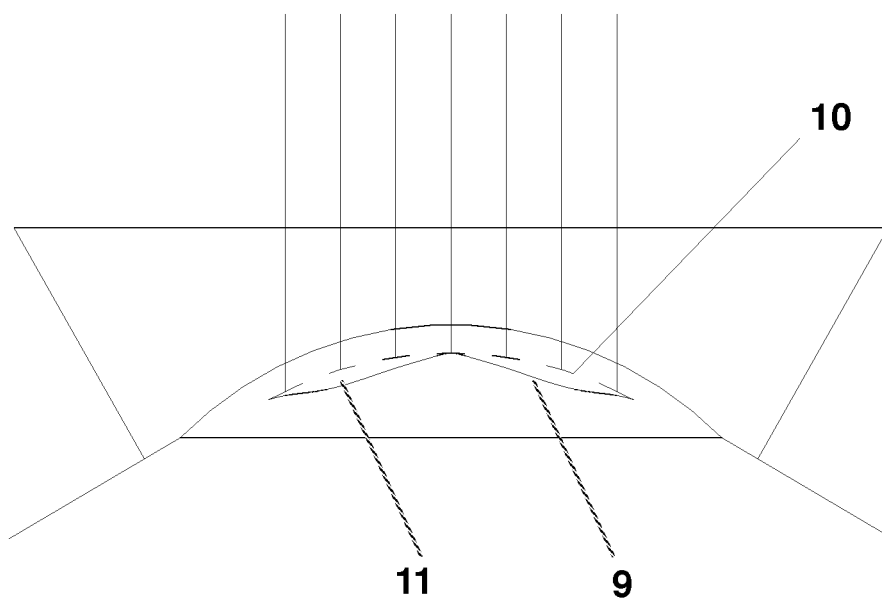
FIG. 10 is a schematic representation of creating the second correcting surface cut into the stroma using a femto-laser beam.

FIG. 10 depicts a second cut or standard cut 10, shown by a dashed line, that is generated via laser radiation as described. The second standard cut 10 is on the top of the first correcting surface cut 9 to produce a lenticule 11 (see FIG. 11).

Figure 11:
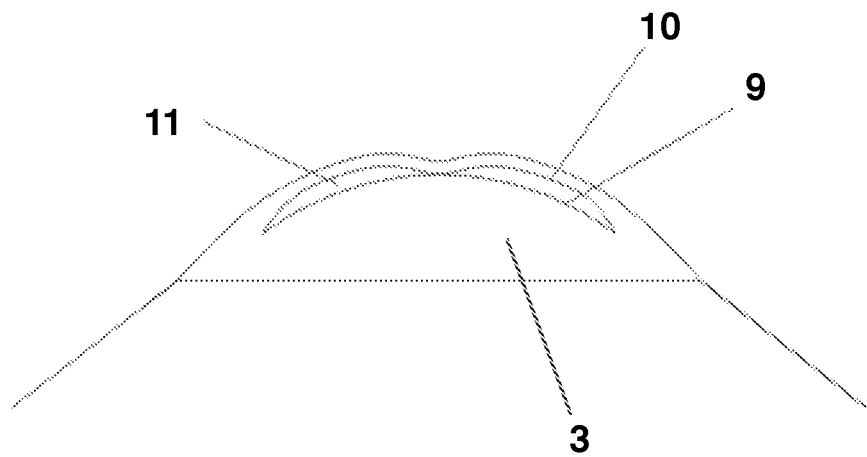
FIG. 11 is a schematic representation of the first and second correcting surface cuts and the intrastromally created lenticule.

FIG. 11 illustrates that after the second flap contact glass 1b is removed from the cornea both the correcting cut surface 9 and the second standard cut 10 confine the desired lenticule 11. For correction of defective eyesight, a corneal lenticel 11 has to be separated from the cornea 3, such that the thus-modified curvature of the anterior corneal surface results in the desired correction of defective eyesight.

Figure 12:
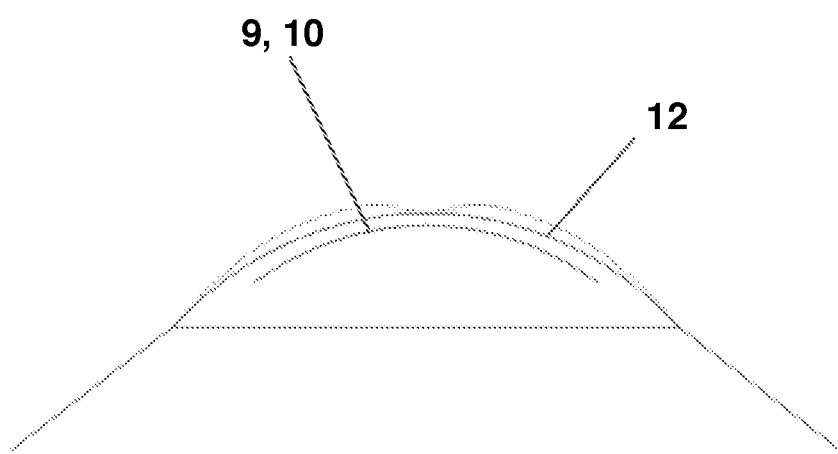
FIG. 12 is a schematic representation of the corneal surface with the corrected curvature.

FIG. 12 depicts the anterior corneal surface 12 after the lenticule is removed from a small incision. After removal the second standard cut surface 10 comes to rest on the first correcting cut surface 9 and forms the anterior corneal surface 12 with the desired curvature so that the correction of defective eyesight is achieved. The profile of the distance between the correcting cut surface and the anterior corneal surface or the reference surface varies patient by patient.

The present invention is well adapted to attain the ends and advantages mentioned as well as those that are inherent therein. The particular embodiments disclosed above are illustrative only, as the present invention may be modified and practiced in different but equivalent manners apparent to those skilled in the field having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A method for smoothing an irregular surface of a cornea in an eye prior to correcting a defect in eyesight during a surgical procedure, comprising the steps of:
    delivering via an applicator a minimum amount of a UV polymerizable gel onto an anterior corneal surface of the eye;
    applying an algorithm to identify a curvature corresponding to a first of two correcting surface cuts to be made on the cornea during the surgical procedure;
    selecting a contact element having a contacting surface curvature corresponding to the curvature identified by the algorithm;
    positioning the contact element on the cornea such that the minimum amount of UV polymerizable gel interfaces with the contacting surface of the contact element and the anterior corneal surface of the eye;
    solidifying the UV polymerizable gel via ultraviolet radiation directed through the contact element as a layer of minimum thickness covering the anterior corneal surface, thereby smoothing irregularities present in the anterior corneal surface, said contact element remaining in position on the layer after solidifying to maintain the curvature for the first cut during the surgical procedure.

2. The method of claim 1, wherein the solidifying step comprises:
    delivering the ultraviolet radiation via an ultraviolet light emitter configured for triggering polymerization of the UV polymerizable gel to form the layer of minimum thickness.

3. The method of claim 2, wherein the ultraviolet light emitter and the applicator are combined in a gel solidifying unit.

4. The method of claim 1, wherein the UV polymerizable gel comprises polyurethane methacrylate (PUMA).

5. The method of claim 1, wherein the UV polymerizable gel comprises a polyester and a catalyst Methyl Ethyl Ketone Peroxide (MEKP).

6. The method of claim 1, wherein the UV polymerizable gel is a hydrogel.

7. The method of claim 1, wherein when a mean corneal index is about 1.4 Diopters, a difference of a corneal refractive index between the cornea and the layer of minimum thickness is less than about 0.5 Diopter.

* * * * *